United States Patent
Park et al.

(10) Patent No.: US 8,724,116 B2
(45) Date of Patent: May 13, 2014

(54) SCANNING MIRRORS IN NEAR FIELD OPTICAL MICROSCOPE HAVING SUPER RESOLUTION

(75) Inventors: Seung-Han Park, Seoul (KR); Dae-Geun Kim, Seoul (KR); Hong-Gyu Ahn, Seoul (KR); Eung-Jang Lee, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 946 days.

(21) Appl. No.: 12/739,266

(22) PCT Filed: Feb. 18, 2008

(86) PCT No.: PCT/KR2008/000939
§ 371 (c)(1),
(2), (4) Date: Jun. 28, 2010

(87) PCT Pub. No.: WO2009/054576
PCT Pub. Date: Apr. 30, 2009

(65) Prior Publication Data
US 2010/0296097 A1    Nov. 25, 2010

(30) Foreign Application Priority Data
Oct. 23, 2007  (KR) ........................ 10-2007-0106744

(51) Int. Cl.
  *G01B 11/02*  (2006.01)
  *G01Q 60/18*  (2010.01)
(52) U.S. Cl.
  USPC ............................................ 356/511; 850/30
(58) Field of Classification Search
  USPC ............. 356/501, 511; 250/458.1; 850/22, 30
  See application file for complete search history.

(56) References Cited

U.S. PATENT DOCUMENTS

| 5,382,789 A | 1/1995 | Aoshima |
| 6,674,057 B1 | 1/2004 | Wiegraebe et al. |
| 7,582,870 B2 * | 9/2009 | Lee et al. .................. 250/338.1 |
| 2010/0141939 A1 * | 6/2010 | Zhan ............................ 356/301 |

FOREIGN PATENT DOCUMENTS

| JP | 07-248203 A | 9/1995 |
| JP | 10-282120 A | 10/1998 |

(Continued)

*Primary Examiner* — Hwa Lee
(74) *Attorney, Agent, or Firm* — Rothwell, Figg, Ernst & Manbeck, P.C.

(57) ABSTRACT

Provided is a scanning optical measurement apparatus having super resolution. The scanning optical measurement apparatus includes: a light source; a first lens, which focuses light irradiated from the light source; a first pin hole, which is disposed next to the first lens; a second lens, which diverges light that passed through the first pin hole; a scanning unit, which scans light that passed through the second lens; a first beam splitter, which is disposed between the second lens and the scanning unit; an object lens, which focuses light that passed through the scanning unit on the subject; a slide, where the subject is placed; an optical probe, which reflects the light that passed through the subject after being irradiated from the light source; a second beam splitter, which is disposed between the scanning unit and the object lens; a first optical detector, which detects the light that passed through the first beam splitter after being reflected from the subject and the optical probe; a second pin hole, which is disposed between the first beam splitter and the first optical detector; and a second optical detector, which detects light that passed through the second beam splitter after being reflected from the subject and the optical probe.

6 Claims, 4 Drawing Sheets

(56) References Cited

FOREIGN PATENT DOCUMENTS

| JP | 10-293133 A | 11/1998 |
| JP | 11-316240 A | 11/1999 |
| JP | 2004-226112 A | 8/2004 |
| JP | 2006-284435 A | 10/2006 |
| KR | 1020050099217 A | 10/2005 |
| WO | 2006083006 A1 | 8/2006 |

* cited by examiner

SCANNING MIRRORS IN NEAR FIELD OPTICAL MICROSCOPE HAVING SUPER RESOLUTION

CROSS REFERENCE TO RELATED APPLICATION(S)

This application is a 35 U.S.C. §371 National Phase Entry Application from PCT/KR2008/000939, filed Feb. 18, 2008, and designating the United States. This application also claims the benefit of Korean Patent Application No. 10-2007-0106744 filed Oct. 23, 2007, the disclosure of which is incorporated herein in its entirety by reference.

TECHNICAL FIELD

The present invention relates to a scanning optical measurement apparatus, and more particularly, to a scanning optical measurement apparatus having super resolution, which quickly scans a relatively large area of a subject, and observes a desired local domain with high resolution.

BACKGROUND ART

Since an optical microscope, which is used to observe an organism, a microelement structure in a nanometer unit, or the shape of a surface, observes an object by using light, the resolution is limited due to a diffraction limit phenomenon. In other words, an object whose size is equal to or lower than ½ of the wavelength of the light cannot be optically observed. Accordingly, a near field optical microscope is developed, which can overcome such a diffraction limit and perform optical measurement at a much lower level than the wavelength of the light. In the near field optical microscope, light that passed through an opening smaller than the wavelength of the light irradiates an examined material that is at a distance similar to the size of the opening. Here, a near field that is at a smaller distance than the wavelength of the light from the surface of the examined material does not generate diffraction. Accordingly, in order to improve the resolution of the near field optical microscope, the size of the opening should be reduced and the distance between the opening and the surface of the examined material should be reduced.

A well known near field optical probe used in such a near field optical microscope is an optical fiber near field optical probe 100 as illustrated in FIG. 1. The optical fiber near field optical probe 100 thinly extends an optical fiber 102 by applying heat, or etches the optical fiber 102 by using a chemical so that the size of one end of the optical fiber 102 of the optical fiber 102 becomes several tens through several hundreds of nanometers. Then, a metal layer 104 is deposited on the optical fiber 102 in order to prevent light from escaping from the external surface of the optical fiber 102, and an opening 105, which has a diameter of several tens through several hundreds of nanometers, is formed at the end of the optical fiber 102. A reference numeral 103 denotes a near field.

In order to measure an optical characteristic of an examined material 106 having a nanostructure by using the optical fiber near field optical probe 100, the optical fiber near field optical probe 100 is drawn near to the examined material 106 in a range of several to several tens of nanometers. Then, an optical signal reflected from each irradiation point is measured while irradiating light onto the surface of the examined material 106, and an entire image is obtained by combining the optical signals.

In order to draw the optical fiber near field optical probe 100 up to a nanometer distance of the examined material 106, the optical fiber near field optical probe 100 is attached to a crystal oscillator 110, and the crystal oscillator 110 is vibrated at a uniform frequency by using a piezo oscillator 113. Then, a vibration signal is applied to the piezo oscillator 113 by using a lock-in amplifier 115. A signal detected from the crystal oscillator 110 changes according to a distance between the optical fiber near field optical probe 100 and the examined material 106. Accordingly, the distance between the optical fiber near field optical probe 100 and the examined material 106 can be adjusted by detecting the signal.

The detected signal is provided to a piezo translator 120 as a feedback signal through the lock-in amplifier 115 and a proportional integrator 117, and the moving amount of the piezo translator 120 is compensated by using the provided signal.

When the optical fiber near field optical probe 100 irradiates light onto the surface of the examined material 106, the detected signal of the crystal oscillator 110 changes according to the minute change of the surface of the examined material 106. Precise height information of the surface of the examined material 106 can be obtained by using such changes in the detected signal.

DETAILED DESCRIPTION OF THE INVENTION

Technical Problem

In order to analyze a biological organism or an examined material having optical phase information, light that passes through the examined material should be analyzed. For example, light intensity distribution can be obtained in the opposite direction of a probe after passing light irradiated from the probe through the examined material.

However, when light is irradiated through an optical probe, the intensity of the light that reaches the end of the optical probe increases, and thus a metal layer coated around the optical probe melts. In this case, the size of an opening increases, and thus the opening can no longer operate as a several nano-sized opening. Meanwhile, when the quantity of light is reduced through an optical fiber in order to prevent the metal layer from melting, a detected signal to noise ratio relatively decreases, and thus the resolution deteriorates.

Technical Solution

The present invention provides a scanning optical measurement apparatus having super resolution, which can quickly scan a relatively large area of a subject, and observe a desired local domain with high resolution.

According to an aspect of the present invention, there is provided a scanning optical measurement apparatus including: a light source; a first lens, which focuses light irradiated from the light source; a first pin hole, which is disposed next to the first lens; a second lens, which diverges light that passed through the first pin hole; a scanning unit, which scans light that passed through the second lens; a first beam splitter, which is disposed between the second lens and the scanning unit; an object lens, which focuses light that passed through the scanning unit on the subject; a slide, where the subject is placed; an optical probe, which reflects the light that passed through the subject after being irradiated from the light source; a second beam splitter, which is disposed between the scanning unit and the object lens; a first optical detector, which detects the light that passed through the first beam splitter after being reflected from the subject and the optical probe; a second pin hole, which is disposed between the first beam splitter and the first optical detector; and a second optical detector, which detects light that passed through the second beam splitter after being reflected from the subject and the optical probe.

The scanning unit may include a Galvano mirror.

The scanning optical measurement apparatus may further include: a first mirror, which is disposed between the first beam splitter and the second lens; a second mirror, which is disposed between the scanning unit and the second beam splitter; and a flip mount, on which the first and second mirrors are installed and which moves the first and second mirrors.

The optical probe may be disposed inside a near field of the subject.

The second optical detector may detect coherent light that is generated as the light reflected from the surface of the subject and the light reflected from the optical probe interfere with each other.

An area where the light that passed through the subject is reflected in the optical probe may have a smaller size than the wavelength of the light that is irradiated form the light source.

The slide may be a nano-slide.

MODE OF THE INVENTION

Hereinafter, the present invention will be described in detail by explaining exemplary embodiments of the invention with reference to the attached drawings.

Figure 1:
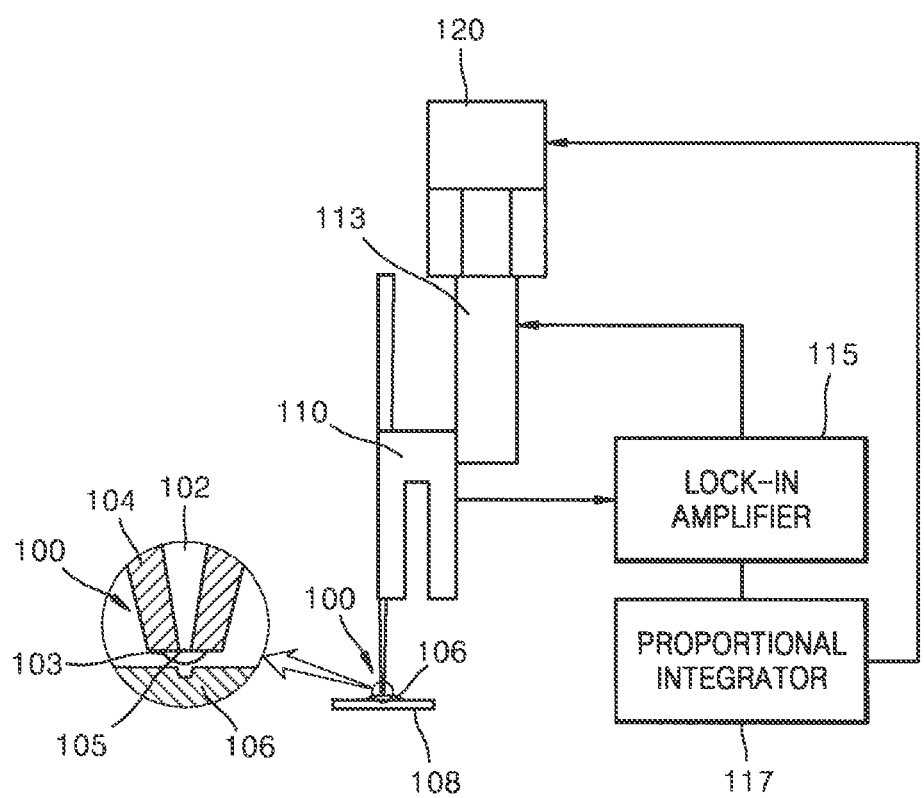
FIG. 1 is a diagram illustrating a conventional scanning optical measurement apparatus.
Figure 2:
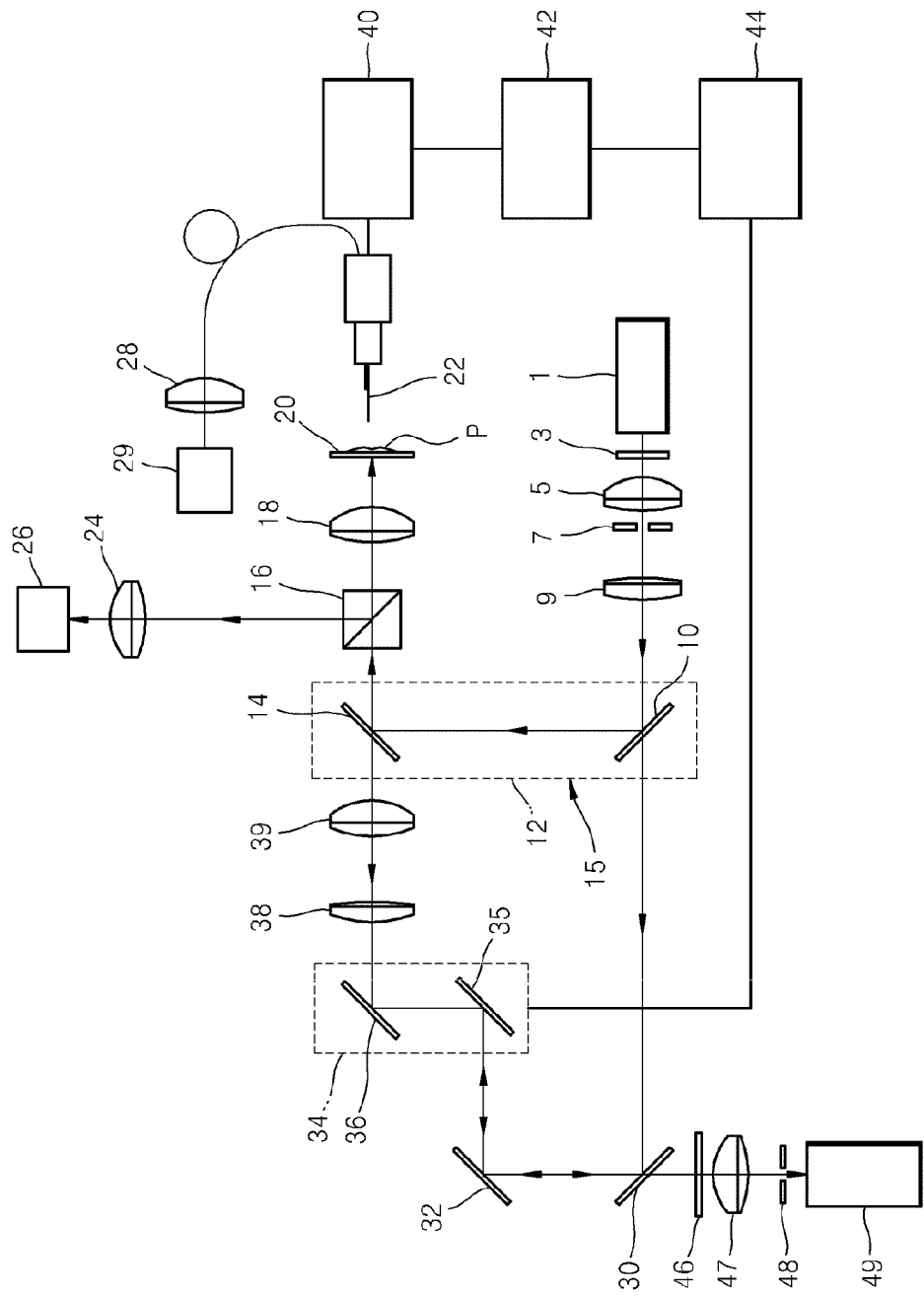
FIG. 2 is a diagram illustrating a scanning optical measurement apparatus according to an embodiment of the present invention.

FIG. 2 is a diagram illustrating a scanning optical measurement apparatus according to an embodiment of the present invention. The scanning optical measurement apparatus includes a light source 1, which irradiates light, a slide 20, where a subject P is placed, and an optical probe 22, which reflects the light that is irradiated from the light source 1 and passed through the subject P. A first beam splitter 30 and a second beam splitter 16, which separate an incident light, are disposed on an optical path between the light source and the slide 20. A first lens 5, which focuses the light irradiated form the light source 1, a first pin hole 7, which is disposed next to the first lens 5, and a second lens 9, which emits the light that passed through the first pin hole 7, may be disposed between the light source 1 and the first beam splitter 30.

The light focused by the first lens 5 is emitted through the first pin hole 7, and is then incident on the second lens 9. The light that passed through the second lens 9 has a larger diameter than a section diameter of the light that is incident on the first lens 5. The light source 1 may be a laser that outputs light in a 650 nm wavelength band, 480 nm wavelength band, or 350 nm wavelength band. For example, the light source 1 may be a He—Ne laser, a Ar laser, or a He—Cd laser. The first beam splitter 30 may be replaced by a dichroic mirror. A shutter 3 may be further included between the light source 1 and the first lens 5. When a white light source is used as light source, the shutter 3 may be used to pass or block a laser beam so as to use white light and the laser beam together or separately.

A scanning unit 34, which scans the light, is disposed between the first and second beam splitters 30 and 16. The scanning unit 34 scans the light irradiated from the light source 1 onto the subject P, so as to quickly observe the large area of the subject P. The scanning unit 34 may include Galvano mirrors 35 and 36. An object lens 18 is disposed between the second beam splitter 16 and the slide 20, and the optical probe 22 is disposed on a path of the light that passed through the slide 20.

A first optical detector 49 is disposed in a back-path of the first beam splitter 30 in order to detect the light that is emitted from the light source 1, passed through the first beam splitter 30, the scanning unit 34, and the object lens 18, reflected off the subject P on the slide 20, and then returned back to the first beam splitter 30. A second optical detector 26 is disposed in a back-path of the second beam splitter 16 in order to detect coherent light where the light reflected at the subject P on the slide 20 and the light reflected at the optical probe 22 interfere with each other. Here, the back-path is a path of the light, which is emitted from the light source 1 and reflected off the subject P. The path is different from the initial path as the light passes through the first and second beam splitters 30 and 16.

A second pin hole 48 is disposed between the first beam splitter and the first optical detector 49. The second pin hole 48 blocks the light that is out of focus, and improves the resolution by only transmitting the light that is in focus to the first optical detector 49. The first optical detector 49 may be a photo multiplication tube (PMT). A lens 47 and a filter 46 may be further disposed between the second pin hole 48 and the first beam splitter 30. The filter 46 may be a neutral density (ND) filter for adjusting the quantity of light. Alternatively, with respect to fluorescent light, the fluorescent light may have several wavelengths, and so the filter 46 may be a band pass filter that only passes light of a certain wavelength.

A first optical path converting unit 32, which converts the path of the light, may be disposed between the first beam splitter 30 and the scanning unit 34 on the optical path. An optical path converting unit may be selectively included considering a geometrical arrangement of an optical system. Meanwhile, a second optical path converting unit 15, which converts a path of the light that passed through the second lens 9, may be further included. The second optical path converting unit 15 may include a first mirror 10, which is disposed between the first beam splitter 30 and the second lens 9, a second mirror 14, which is disposed between the scanning unit 34 and the second beam splitter 16, and a flip mount 12, where the first and second mirrors 10 and 14 are installed and which can move the first and second mirrors 10 and 14. The flip mount 12 may move the first and second mirrors 10 and 14 so as to locate them on an optical axis or outside the optical axis.

When the second optical path converting unit 15 is disposed on the optical axis, the light emitted from the light source 1 is incident on the subject P by directly passing through the slide 20 without passing through the scanning unit 34. When the second optical path converting unit 15 is outside the optical axis, the light emitted from the light source 1 is incident on the slide 20 after passing through the first beam splitter 30 and the scanning unit 34.

At least one lens (in FIG. 2, two lenses 38 and 39) may be further disposed between the scanning unit 34 and the second beam splitter 16. The scanning optical measurement apparatus according to the current embodiment of the present invention can quickly observe a large area of the subject P through the first optical detector 49 by scanning the subject P by using the scanning unit 34. Here, the resolution is improved by measuring the subject P as the first optical detector 49 only receives the light that is in focus through the second pin hole 49. Accordingly, the large area of the subject P can be measured, and an image of a desired certain area is detected by the second optical detector 26. The second optical detector 26 detects the coherent light, where light reflected off the subject P on the slide 20, and light reflected at the optical probe 22 after the light emitted from the light source 1 that passes through the first lens 5, the first pin hole 7, and the second lens 9 interfere with each other.

The optical probe 22 may be a reflective probe, which reflects the light that passed through the subject P, such as an optical fiber. The optical probe 22 is located inside a near field range of the subject P. Also, a reflective area of the optical probe 22 may have a smaller size than the wavelength of the light emitted from the light source 1. When the reflective area of the optical probe 22 is smaller than the wavelength of used light, light reflected at the optical probe 22 can be used as a point source. Accordingly, an aberration problem that may be generated in the light reflected at the reflective area may be resolved. Also, the optical probe 22 does not need a separate light source, and thus manufacturing costs are reduced and the scanning optical measurement apparatus is simplified.

The light emitted from the light source 1 passes through the object lens 18, generating a first light reflected off the subject P and a second light reflected from the optical probe 22 to interfere with each other. Such coherent light is reflected at the second beam splitter 16, and is incident on the second optical detector 26. The second optical detector 26 measures the quantity of the coherent light. The quantity of the coherent light changes according to an internal structure or an optical characteristic of the subject P. By detecting the change of the quantity, a change of a refraction rate of the subject P can be measured, and phase information according to the change of the refraction rate can be determined.

As described above, a characteristic of a subject is measured by using coherent light by a reflective optical probe, and thus a minute change in the shape or internal structure of the subject can be sensitively measured and observed.

Meanwhile, the optical probe 22 can not only reflect the incident light but also pass the incident light. Accordingly, the light that passed through the subject P may be passed through the optical probe 22. The quantity of the light that passed through the optical probe 22 is measured by a third optical detector 29, and thus a change of a transmission rate and an optical spectrum of the subject P can be measured. Accordingly, change of an absorptance rate of the subject P can be analyzed.

The surface shape of the subject P can be measured according to principles of a near field scanning microscope by locating the optical probe 22 within a near field range of the subject P. A lens 24 may be further disposed between the second beam splitter 16 and the second optical detector 26, and a lens 29 may be further disposed between the optical probe 22 and the third optical detector 29. A first controller 40 controls the optical probe 22 to scan a local area, and a second controller 44 controls the scanning unit 34. The first and second controllers 40 and 44 are operated by a computer 42.

Figure 3:
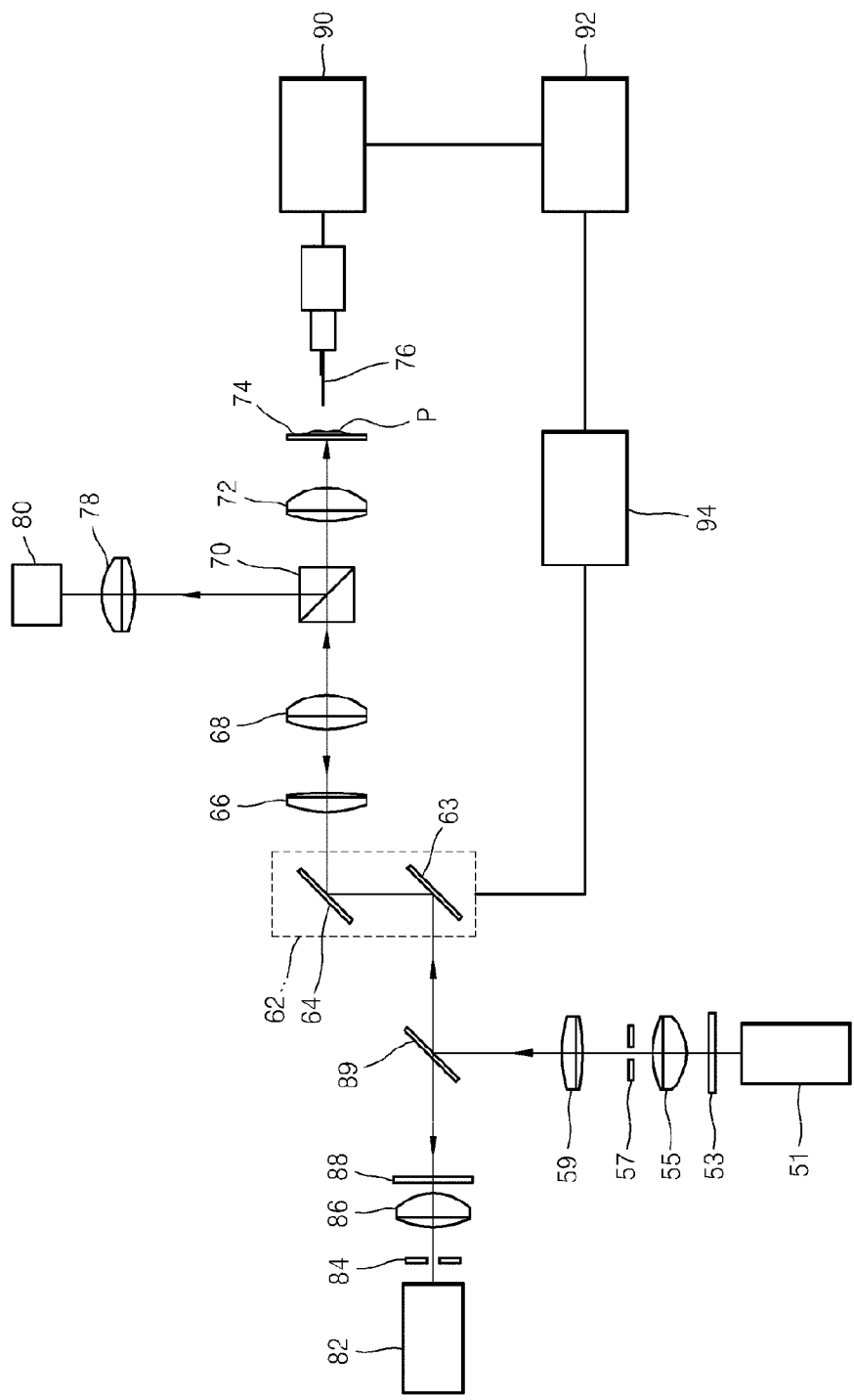
FIG. 3 is a diagram illustrating a scanning optical measurement apparatus according to another embodiment of the present invention.

FIG. 3 is a diagram illustrating a scanning optical measurement apparatus according to another embodiment of the present invention. The scanning optical measurement apparatus includes a light source 51, a first beam splitter 89 which separates light emitted from the light source 51, a scanning unit 62 which scans the light, a second beam splitter 70, an object lens 72, a slide 74 where a subject P is placed, and an optical probe 76.

A first lens 55 and a second lens 59 are disposed between the light source 51 and the first beam splitter 89, and a first pin hole 57 is disposed between the first and second lenses 55 and 59. A shutter 53 may be further disposed between the light source 51 and the first lens 55. The scanning unit 62 may include a Galvano mirror, including a first mirror 63 and a second mirror 64. At least one (in FIG. 3, two lenses 66 and 68) may be disposed between the scanning unit 62 and the second beam splitter 70. The at least one lens may be a scan lens or a tube lens.

A first optical detector 82 is included so as to detect the light that passed through the first beam splitter 89 after being reflected off the subject P. A second pin hole 84, a lens 86, and a filter 88 may be included between the first optical detector 82 and the first beam splitter 89. The resolution is improved as the second pin hole 84 passes the light that is in focus through an aperture and blocks the light that is out of focus. Coherent light, where the light reflected off the subject P and the light reflected at the optical probe 76 interfere with each other, is reflected at the second beam splitter 70 and is detected by the second optical detector 80. A lens 78 may be further disposed between the second beam splitter 70 and the second optical detector 80.

The scanning unit 62 scans a large area of the subject P, and an image obtained during the scanning may be detected by the first optical detector 82. The second optical detector 80, which uses the coherent light, can obtain more detailed information about the subject P. When the second optical detector 80 obtains optical information of the subject P, the scanning unit 62 does not operate. Also, a first controller 90 for controlling the optical probe 76 and a second controller 94 for controlling the scanning unit 62 are further included, and the first and second controllers 90 and 94 are operated by a computer 92.

Figure 4:
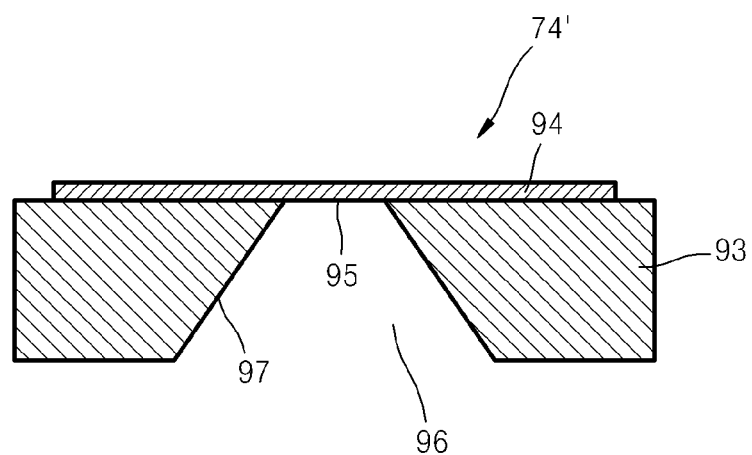
FIG. 4 is a diagram illustrating a nano-slide included in a scanning optical measurement apparatus according to an embodiment of the present invention.

FIG. 4 is a diagram illustrating a nano-slide 74' included in a scanning optical measurement apparatus according to an embodiment of the present invention. The nano-slide 74' is formed of a base 93, an opening 95 having a width of a nanometer unit on the base 93, and a slide board 94 having a thickness of a nanometer unit that covers at least the opening 95.

A through hole 97 whose width gets narrow toward the top is formed in the base 93. The opening 95 is formed on the top of the through hole 97 and an entrance 96 that is larger than the opening 95 is formed on the bottom of the through hole 97. For example, the through hole 97 may have a truncated pyramid shape.

The slide board 94 is formed on the base 93 to at least cover the opening 95, and is formed of an optically transparent material. For example, the slide board 94 may be formed of $Si_3N_4$ and have a thickness of a nanometer unit. When the nano-slide 74' is used, the resolution is improved, and a subject may be placed inside or outside the slide board 94. When the subject is placed outside the slide board 94, and both surface information and phase information of the subject can be obtained by moving an optical probe along the surface of the subject.

The invention claimed is:
1. A scanning optical measurement apparatus comprising:
a light source;
a first lens, which focuses light irradiated from the light source;
a first pin hole, which is disposed next to the first lens;

a second lens, which diverges light that passed through the first pin hole;

a scanning unit, which scans light that passed through the second lens;

a first beam splitter, which is disposed between the second lens and the scanning unit;

an object lens, which focuses light that passed through the scanning unit on the subject;

a slide, where the subject is placed;

an optical probe, which reflects the light that passed through the subject after being irradiated from the light source;

a second beam splitter, which is disposed between the scanning unit and the object lens;

a first optical detector, which detects the light that passed through the scanning unit and the first beam splitter after being reflected from the subject and the optical probe;

a second pin hole, which is disposed between the first beam splitter and the first optical detector;

second optical detector, which detects light that passed through the second beam splitter after being reflected from the subject and the optical probe, wherein light reflected from the subject and light reflected from the optical probe interfere with each other;

a first mirror, which is disposed between the first beam splitter and the second lens;

a second mirror, which is disposed between the scanning unit and the second beam splitter; and a flip mount, on which the first and second mirrors are installed and which moves the first and second mirrors.

2. The scanning optical measurement apparatus of claim 1, wherein the scanning unit comprises a Galvano mirror.

3. The scanning optical measurement apparatus of any one of claims 1 through 2, wherein the optical probe is disposed inside a near field of the subject.

4. The scanning optical measurement apparatus of any one of claims 1 through 2, wherein the second optical detector detects coherent light that is generated as the light reflected from the surface of the subject and the light reflected from the optical probe interfere with each other.

5. The scanning optical measurement apparatus of any one of claims 1 through 2, wherein an area where the light that passed through the subject is reflected in the optical probe has a smaller size than the wavelength of the light that is irradiated form the light source.

6. The scanning optical measurement apparatus of any one of claims 1 through 2, wherein the slide is a nano-slide.

\* \* \* \* \*